(12) United States Patent
Neumann

(10) Patent No.: US 11,931,186 B2
(45) Date of Patent: *Mar. 19, 2024

(54) METHOD OF SYSTEM FOR REVERSING INFLAMMATION IN A USER

(71) Applicant: KPN INNOVATIONS, LLC., Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/517,801

(22) Filed: Nov. 3, 2021

(65) Prior Publication Data
US 2022/0061772 A1  Mar. 3, 2022

Related U.S. Application Data

(63) Continuation of application No. 17/007,251, filed on Aug. 31, 2020, now Pat. No. 11,179,110.

(51) Int. Cl.
| | |
|---|---|
| *A61B 5/00* | (2006.01) |
| *A61B 90/00* | (2016.01) |
| *G06N 20/00* | (2019.01) |
| *G16H 20/60* | (2018.01) |
| *G16H 40/63* | (2018.01) |

(52) U.S. Cl.
CPC .............. *A61B 5/7267* (2013.01); *A61B 5/48* (2013.01); *A61B 5/7246* (2013.01); *A61B 5/7435* (2013.01); *A61B 90/39* (2016.02); *G06N 20/00* (2019.01); *G16H 20/60* (2018.01); *G16H 40/63* (2018.01)

(58) Field of Classification Search
CPC ........ G16H 50/00; G16H 50/20; G16H 50/30; G16H 50/50
See application file for complete search history.

*Primary Examiner* — Scott Luan
(74) *Attorney, Agent, or Firm* — Caldwell Intellectual Property Law

(57) ABSTRACT

A system for reversing inflammation in a user, wherein the system further comprises a computing device further designed and configured to receive a physiological extraction of a user, wherein the physiological extraction contains at least an inflammation marker, generate, using an inflammation machine-learning model and the user physiological extraction input, a first inflammation metric of a user, wherein generating the first inflammation metric further comprises training an inflammation machine-learning model as a function of inflammation metric training data, wherein the inflammation metric training data includes a plurality of entries, and each entry correlates user physiological extraction data to at least an inflammation metric that quantitates hallmarks of inflammation in the user, identify, using an alimentary element machine-learning process and the first inflammation metric, at least an alimentary element for reversing inflammation in the user, and provide, to the user, the at least an alimentary element for reversing inflammation.

20 Claims, 8 Drawing Sheets

METHOD OF SYSTEM FOR REVERSING INFLAMMATION IN A USER

CROSS-REFERENCE TO RELATED APPLICATIONS

This application is a continuation of Non-provisional application Ser. No. 17/007,251, filed on Aug. 31, 2020, and entitled "METHOD OF SYSTEM FOR REVERSING INFLAMMATION IN A USER" the entirety of which is incorporated herein by reference.

FIELD OF THE INVENTION

The present invention generally relates to the field of machine-learning. In particular, the present invention is directed to methods and systems for reversing inflammation in a user.

BACKGROUND

Worldwide, 3 in 5 people perish due to chronic inflammatory diseases like stroke, respiratory disease, heart disorder, cancers, obesity, and diabetes. Efficient method for identifying and developing strategies to identify and reverse inflammation in users is hindered by diversity in individual cohorts. Moreover, lifestyle preferences and difficulty in changing those preferences complicate adherence to strategies for reducing and reversing inflammation.

SUMMARY OF THE DISCLOSURE

In an aspect, a system for reversing inflammation in a user includes a computing device designed and configured to receive a physiological extraction of a user, wherein the physiological extraction contains at least an inflammation marker, generate, using an inflammation machine-learning model and the user physiological extraction input, a first inflammation metric of a user, wherein generating the first inflammation metric includes training an inflammation machine-learning model as a function of inflammation metric training data, wherein the inflammation metric training data includes a plurality of entries, and each entry correlates user physiological extraction data to at least an inflammation metric that quantitates hallmarks of inflammation in the user, identify, using an alimentary element machine-learning process and the first inflammation metric, at least an alimentary element for reversing inflammation in the user, and provide, to the user, the at least an alimentary element for reversing inflammation.

In another aspect, a method for reversing inflammation in a user includes a computing device designed and configured for receiving a physiological extraction of a user, wherein the physiological extraction contains at least an inflammation marker, generating, using an inflammation machine-learning model and the user physiological extraction input, a first inflammation metric of a user, wherein generating the first inflammation metric includes training an inflammation machine-learning model as a function of inflammation metric training data, wherein the inflammation metric training data includes a plurality of entries, and each entry correlates user physiological extraction data to at least an inflammation metric that quantitates hallmarks of inflammation in the user, identifying, using an alimentary element machine-learning process and the first inflammation metric, at least an alimentary element for reversing inflammation in the user, and providing, to the user, the at least an alimentary element for reversing inflammation.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for reversing inflammation in a user. In an embodiment, system includes a computing device designed and configured to receive physiological extraction of a user, wherein physiological extraction contains at least an inflammation marker. Computing device may use a machine-learning model to generate inflammation metrics of a user, wherein the model can differentiate between types of inflammation markers and assign quantitative metrics to the user for their overall inflammation. System may identify, according to the inflammation metric, at least an alimentary element for reversing inflammation and potentially reverse inflammation in the user. In an embodiment, system may provide, to the user, an alimentary element for reversing inflammation, and accept inputs from the user regarding alimentary elements, and suggest alimentary elements based on the effect it would have on the inflammation metric, providing a recipe for potentially using the alimentary elements. Alternatively or additionally, exemplary embodiments may accept inflammation metrics for a plurality of users and suggest an alimentary element and recipe for using that alimentary element, wherein the recipe would improve inflammation metrics in the plurality of users.

Figure 1:
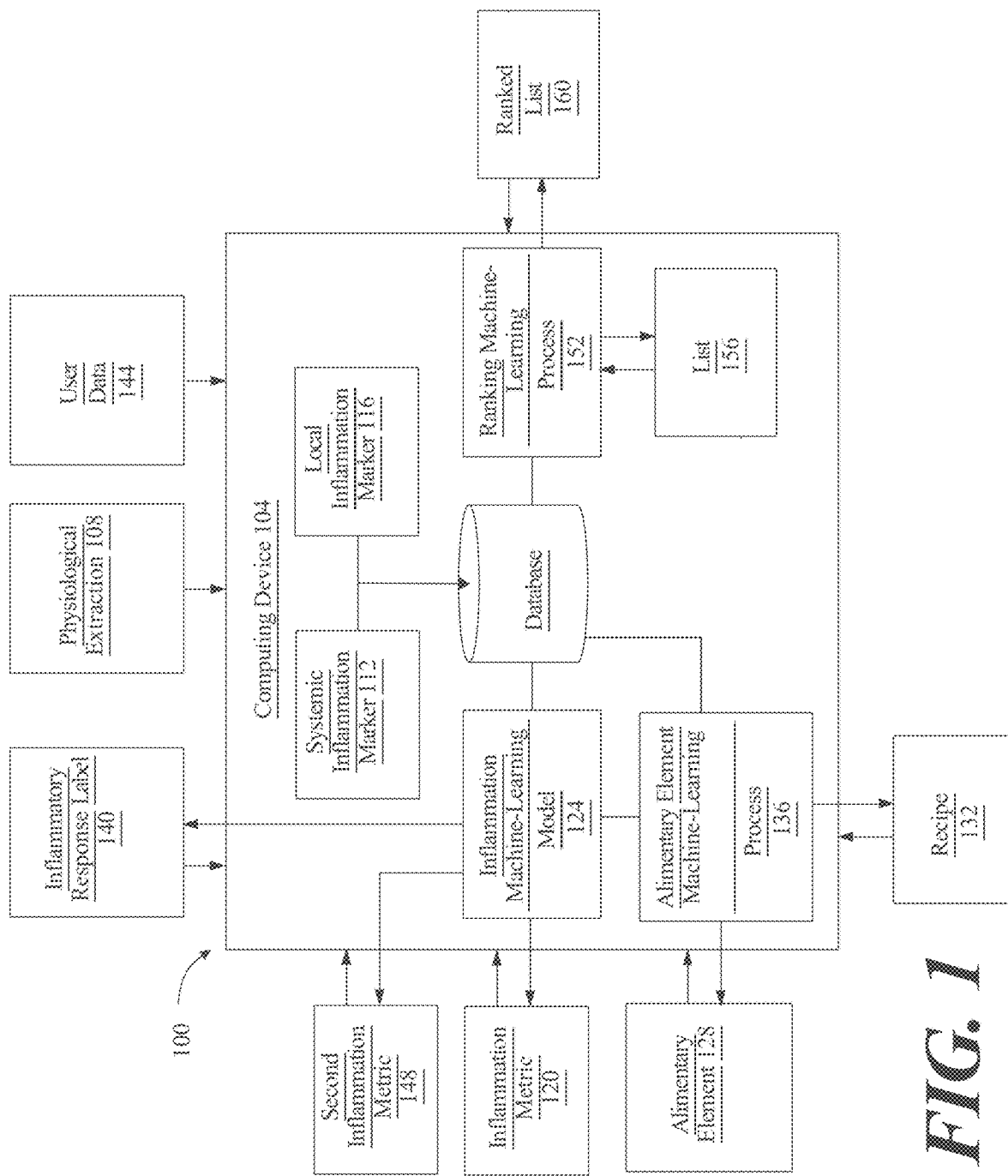
FIG. 1 is a block diagram illustrating an exemplary embodiment of a system of reversing inflammation in a user.

Referring now to FIG. 1, an exemplary embodiment of a system 100 for reversing inflammation in a user is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 is further designed and configured to receive physiological extraction of a user. "Physiological extraction" as used in this disclosure is any element of biological extraction data, wherein biological extraction data refers to any biomarker, genetic data or epigenetic indication, microbiome, or any chemical, biological, or physiological markers of data of a user, including for instance, and without limitation, as described in U.S. Nonprovisional application Ser. No. 16/885,647, filed on Jul. 22, 2020, and entitled "METHODS AND SYSTEMS FOR DETERMINING A PLURALITY OF DIMENSIONS OF BIOLOGICAL EXTRACTION USER DATA AND ARTIFICIAL INTELLIGENCE," the entirety of which is incorporated herein by reference.

Still referring to FIG. 1, physiological extraction 108 may refer to blood chemistry, for instance blood protein and enzyme concentrations and activities for instance of fibrinogen, ferritin, serum amyloid A, α-1-acid glycoprotein, ceruloplasmin, hepcidin, haptoglobin, tumor necrosis factor-α (TNF-α), among other acute phase proteins; for instance cytokine identities and concentrations for instance interleukin-6 (IL-6); blood metabolites identifies and concentrations such as blood sugar, LDL and HDL cholesterol content; hormones identities and concentrations such as insulin, androgens, cortisol, thyroid hormones, and the like; erythrocyte sedimentation rate, blood cell counts, plasma viscosity, and other biochemical, biophysical, and physiological properties regarding blood panels, blood tests, and the like, as it relates to biomarkers of inflammation.

Continuing to refer to FIG. 1, physiological extraction 108 may refer to data concerning genetics of a user and epigenetic analysis, for instance as derived from a physical biological sample derived from hair, skin, saliva, and the like. Epigenetic analysis of inflammation may include enumeration of DNA methylation, acetylation, and other post-translational modifications, presence and concentration of regulatory factors, small non-coding RNAs, and the like.

Continuing to refer to FIG. 1, physiological extraction 108 may include medical history information including, for instance and without limitation, diagnoses, medications, conditions, mental and physical evaluations, and the like. Medical history information may include gut wall strength evaluations among other physical health data, may include a history of surgeries that may be important to inflammation, for instance reconstructions, plastic surgeries, use of prosthetics, and the like. Medical history information may include current and past medications, including over-the-counter remedies and medications, for instance and without limitation non-steroidal anti-inflammatory drugs (NSAIDs).

Still referring to FIG. 1, physiological extraction 108 may include microbiome data that describes, for instance, identities, amounts, chemical signatures, metabolites, signaling peptides, and the like, of bacteria, fungi, protists, parasites, viruses, and other microbiological entities and organisms that may provide information about a user's inflammation.

Continuing to refer to FIG. 1, physiological extraction 108 may include data regarding exposure to environmental factors including chemicals, inhalational irritants, pollen, exposure to allergens, fibers, spores, and the like. Environmental factors present in physiological extraction that may contribute to inflammation may include housing integrity factors such as the presence of leaded products, asbestos, mold, and the like.

Continuing to refer to FIG. 1, physiological extraction 108 may include user lifestyle data such as sleep patterns, duration, and schedules, diet and food selections, supplements, exercise frequency, duration, activities, and the like. Persons skilled in the art, upon review of this disclosure in its entirety, will be aware of the types of data of a user that may be used as physiological extraction for purposes described herein.

Continuing to refer to FIG. 1, physiological extraction 108 of a user contains at least an inflammation marker. An "inflammation marker," as used in this disclosure is a physiological element indicative of diagnosing and/or monitoring inflammatory conditions. Inflammatory markers may be indicative of and/or associated with inflammatory conditions, for instance and without limitation, infections, autoimmune conditions, cancers, physical exertion, sleep deprivation, among many other conditions. At least an inflammation marker may include a systemic inflammation marker. As used in this disclosure "systemic inflammation marker" is a marker indicative of a background level of chronic inflammation present in a user. For instance and without limitation, systemic inflammation marker 112 may relate to C-reactive protein (CRP) concentration and oligomeric state identified from a user blood sample, erythrocyte sedimentation rate (ESR), procalcitonin (PCT) concentration, and the like, that may not be related to any particular disease, injury, trauma, among other diagnosable conditions. In further non-limiting illustrative examples, systemic inflammation markers may be hormonal profiles, liver function tests for aspartate transaminase (AST), alanine transaminase (ALT), total protein level and albumin content, and the like that may signify chronic inflammation from exercise, tissue damage, longstanding injury, repetitive motion, and the like. Systemic inflammation marker 112 may relate to a general level of inflammation in a user that may subsist despite no known underlying tissue damage, injury and/or trauma. A user with a clinical manifestation that is otherwise normal may have measurable background markers of inflammation that are a part of normal physiology. These markers, such as those described above, may be systemic inflammation markers 112 of a user's basal, background level of inflammation.

Continuing in reference to FIG. 1, at least an inflammation marker may include a local inflammation marker. As used in this disclosure "local inflammation marker" is a marker indicating a localized level of acute inflammation present in a user. For instance and without limitation, local inflammation marker 112 may refer to biomarkers associated with acute injury, infection, trauma, and diseases, such as a soft-tissue injury, temporary condition, curable or addressable condition. In non-limiting illustrative examples, localized aggressive periodontitis (LAP) is a condition in users that can be measured by assessing a physical gingival crevicular fluid (GCF) sample and evaluating for the presence of and concentrations of proteins, enzymes, cytokines, and other signaling molecules. In such an example, common local inflammatory markers 116 may be (TNF-α), IL-1β, IL-2, IL-4, IL-6, IL-8, IL-10, IL12p40, granulocyte-macrophage colony-stimulating factor (GMCSF), monocyte chemoattractant protein-1 (MCP-1), among other factors. Moreover, in users affected by LAP, microbiome data regarding endotoxin concentration from bacteria present in the mouth, nose, throat, sinus, and the like, may be 4-5+ times higher than those who do not suffer from LAP, wherein proportions of endotoxin protein concentration may be a local inflammation marker 116 caused by bacterial infections.

Continuing in reference to FIG. 1, computing device 104 may generate an inflammation metric of a user, wherein generating the inflammation metric may include using an inflammation machine-learning model, the inflammation machine-learning model may be trained using training data that enumerates hallmarks of inflammation in a user with quantitative measurements of inflammation. An "inflammation metric," as used in this disclosure, is a quantitative value that describes systemic and/or local inflammation of a user, including any identified sources of inflammation. An inflammation metric 120 may be expressed as a numerical value, function, vector, matrix, or any other suitable form of organizing quantitative data relating to a user's systemic and local inflammation as determined by their physiological extraction 108 data. An inflammation machine-learning model may be any suitable machine-learning algorithm or process that may be performed by a machine-learning module, as described in further detail below.

Inflammation machine-learning model 124 may train with training data that corresponds to, for instance and without limitation, healthy and/or normal physiological levels of inflammation markers, wherein the normal range is associated with a numerical score, for instance as a percentile score, and a user's inflammation marker level corresponds to a numerical value relative the range of scores in the model. In such an example, the inflammation machine-learning model 124 may perform this function for each inflammation marker identified in the user physiological extraction 108 data. In non-limiting exemplary embodiments, a user may have hundreds of pieces of inflammation data present in their physiological extraction that may relate to known healthy ranges of inflammation markers that can be related to some quantitative scale. In non-limiting illustrative examples, the inflammation machine-learning model 124 may locate and train with data that indicates a normal range of IL-6 may be 0-16.4 picograms/milliliter (pg/mL) with a mean of 6.0 pg/mL wherein the mean is set of a nominal score of '0' and the lower limit of 0 pg/mL, indicating no inflammatory marker present in a healthy individual showing no IL-6 indication of inflammation may be set of a score of +10, with negative scores for IL-6 concentrations above the mean. In such an example, having maximal scores for other inflammation markers may be impacted by negative values of <−10 for inflammation marker concentrations that exceed upper ranges found in healthy, normal, and even non-healthy, abnormal individuals. In this manner of scoring, having a concerningly high level of inflammation marker in one category may negate the score of having no inflammatory markers in another marker category. It is important to note that the inflammation machine-learning model 124 may train using a large quantity of inflammation marker ranges depending on input user inflammation markers.

Continuing in reference to FIG. 1, computing device 104 identifies, as a function of the inflammation metric, at least an alimentary element for reversing inflammation in the user. An "alimentary element," as used in this disclosure, is a food item, supplement, nutrient, or the like that a person may eat, take, or otherwise consume as part of a diet, dietary supplement, or the like. An alimentary element 128 may be a food item such as a fruit, vegetable, or dairy product; alternatively or additionally an alimentary element may be a spice, cooking ingredient, probiotic, or the like, such as *echinacea*, onion powder, oils such as avocado oil and mineral oil, plant extracts such as vanilla extract, wintergreen extract, probiotics, and the like. Alimentary element 128 may be a macronutrient or supplement such as branched chain amino acids (BCAAs), proteins such as whey protein, casein protein, enzymes such as lipase, carbohydrates such as dietary fiber and inulin, among other dietary supplements. An alimentary element 128 may be considered a complete meal or food item that can be consumed on its own, and/or as an ingredient or component of a dish and/or meal, wherein the ingredient may require preparation or is intended to be used with a plurality of alimentary elements.

Continuing in reference to FIG. 1, computing device 104 determining the at least an alimentary element 128 for the user may include using the computing device 104 to query for a suitable alimentary element 128 for reversing inflammation in the user as a function of the at least an inflammation marker. A "suitable alimentary element," as used in this disclosure, is an alimentary element for reversing inflammation in the user, where the alimentary element does not negatively impact the user, for instance by triggering an allergy as determined from physiological extraction. Computing device 104 may query for a suitable alimentary element by accepting an input of the user inflammation level as a guide to query for alimentary elements that may reduce the inflammation metric of a user. Computing device 104 may query using an online internet web browser, peer-reviewed research, medical journals, clinical research, expert submission, SQL server, relational database, or the like, as described in further detail below. Computing device 104 may generate an output of alimentary elements for reversing inflammation in specific metrics of a user after a query related to the inflammation metric of the user. Persons skilled in the art, upon review of this disclosure in full, will be aware of the various ways in which a computing device may query sources of information using textual submission.

Continuing in reference to FIG. 1, computing device 104 querying for a suitable alimentary element 128 may include using the alimentary element machine-learning process to retrieve at least a recipe for the suitable alimentary element 128, wherein the recipe reduces the at least an inflammation marker. A "recipe," as used in this disclosure, is a series of steps and/or instructions regarding a list of ingredients and methods for preparing a meal using the indicated ingredients. Computing device 104 querying for an alimentary element 128 for reversing the inflammation metric 120 of user may include locating and retrieving a recipe 132 for using an alimentary element 128, wherein all elements—including ingredients, cooking oils, spices, and the like—are compatible with a user's inflammation metric 120. An alimentary element machine-learning process may be any suitable machine-learning algorithm or process that may be performed by a machine-learning module, as described in further detail below. Computing device 104 may query for the recipe in the same manner as querying an alimentary element 128; alternatively or additionally computing device 104 may use the alimentary element machine-learning process 136 to query and retrieve recipe 132. Alimentary element machine-learning process 136 may accept an input of a plurality of alimentary elements 128 that were previously queried to build, construct, or otherwise generate a recipe using the alimentary elements 128. Alimentary element machine-learning process 136 may accept an input that is a single alimentary element 128 and retrieve recipes including additional alimentary elements, cross-checking each individual ingredient for its potential effect on inflammation metric 120, wherein additional alimentary elements that may contribute to inflammation may be swapped, or otherwise changed to either a new alimentary element, or omitted from the recipe. Alimentary elements 128 and/or recipes 132 compatible with a user inflammation metric 120 may be stored and/or retrieved by the alimentary element machine-learning process from a database, as described in further detail below, wherein the machine-learning process learns what options are best for an individual.

Continuing in reference to FIG. 1, computing device 104 provides a representation of the at least an alimentary element 128 for reversing inflammation within a graphical user interface. Computing device 104 may be a user device. User device may be any device suitable for displaying text, graphics, and the like, such as a "smartphone", laptop, or any other suitable device. User device may be interactive wherein user device may display a suggestion and a user may select or input information based upon the suggestion. User device may provide a representation of the at least an alimentary element 128 to the user within a graphical user interface (GUI), wherein the GUI may display text, graphics, metrics, or any other outputs generated by system 100. Persons skilled in the art, upon review of this disclosure in its entirety, will be aware of the various device that may be suitable as a user device and the various methods of displaying alimentary elements, recipes, inflammation metrics, and the like via graphical user interface.

Continuing in reference to FIG. 1, computing device 104 providing to the user the at least an alimentary element 128 for reversing inflammation may include conveying the at least an alimentary element amount to a user device and receiving a user input from the user device. Computing device 104 may communicate an amount of the alimentary element 128 for reversing inflammation, wherein the amount is a minimal quantity for the anti-inflammatory effect. In non-limiting illustrative examples, an amount may be a single serving, for instance a piece of fruit, such as an apple. In other non-limiting illustrative examples, an amount may be a total mass, a dosage, frequency, or the like, for instance where the alimentary element 128 is a supplement. User device may receive, from a user, an input. An input may be a user selecting an alimentary element 128 so that system 100 may know how the user's inflammation metric 120 will change. An input received from a user may be an alimentary element the user intends to consume, wherein system 100 may suggest an alternative alimentary element 128.

Computing device 104 receiving a user input may receive, from the user device, a first alimentary element and determine, using the inflammation machine-learning model 124 and the first alimentary element, the effect of the first alimentary element on the inflammation metric 120 of the user; and generating an inflammatory response label as a function of determining the affect. An "inflammatory response label," as used in this disclosure is a label indicating a qualitative and/or quantitative effect on an inflammatory metric 120 that can be determined for a food item, meal, supplement, or the like, consumed by a user. In non-limiting illustrative examples, inflammation machine-learning model may accept an input of a first alimentary element and an inflammation metric 120, determine an output that describes how at least an inflammation marker, and thus inflammation metric 120, is affected by a first alimentary element. Such an output may be an inflammatory response label 140. An inflammatory response label 140 may be a predictive measure of how a first alimentary element may affect a user's inflammation. An inflammatory response label 140 may be a numerical value such as a percent of change due to a first alimentary element, wherein the percent change may be from a one-time use of the alimentary element, from sustained used over time, or any other pattern of use indicated by a user.

Continuing in reference to FIG. 1, computing device 104 may be configured to receive a plurality of inflammation metrics, establish at least an alimentary element for reversing inflammation in the plurality of inflammation measurements, generate, by querying a database, at least a recipe for the plurality of alimentary components that do not contribute to inflammation in the plurality of inflammation measurements, and provide, to the user, the recipe. As used herein, "plurality of inflammation metrics" refers to a plurality of inflammation metrics, wherein there may be a plurality of individuals, each with an inflammation metric. In such an instance, computing device 104 may accept an input of the plurality of inflammation metrics and generate an output which is a recipe, wherein the recipe contains alimentary elements that reduce the plurality of inflammation metrics of the individuals. In non-limiting exemplary embodiments, computing device 104 may use the alimentary element machine-learning process 136 to query for and retrieve alimentary elements that may reduce the inflammation metrics of each person, removing alimentary elements that may contribute to inflammation in a person. Computing device 104 may query a database for the alimentary elements, as described in further detail below. The alimentary element machine-learning process 136 may then compile a list of alimentary elements that reduce inflammation of at least an inflammation metric, and also do not contribute to increasing inflammation in any individual, and then query for at least a recipe that uses the alimentary elements, as described above for a single user.

Computing device 104 using the alimentary element machine-learning process 136 may use inflammation machine-learning model 124 to determine how each alimentary element will affect the inflammation markers of a user, and thus the inflammation metric. Computing device 104 may store and/or retrieve recipes, alimentary elements, inflammation metrics, inflammation markers, heuristics, relationships, and other qualitative and quantitative data in determining recipes for a plurality of inflammation metrics. Computing device 104 may provide, to the user, the recipe via a user action, as described in further detail below.

Continuing in reference to FIG. 1, computing device 104 may receive user data, wherein user data may be more current in time than a first provided alimentary element and contains at least an alimentary element selected by the user, generate, using the inflammation machine-learning model and the user data, a second inflammation metric. "User data" as used herein is any alimentary element and/or recipe a user has input via a user device, wherein the data was input by the user after a first inflammation metric was provided to the user. Additionally, user data may include any physiological extraction data of a user more recent than a first physiological extraction datum provided by the user. Computing device 104 may generate using the inflammation machine-learning model trained to recognize correlations between alimentary elements and inflammation markers in a user and determine a second inflammation metric. Computing device 104 may accept inputs of updated user data 144 and retrieve a first inflammation metric 120 of a user and generate an output which is a second inflammation metric 148, wherein the second inflammation metric 148 reflects any changes in inflammation due to alimentary elements consumed by a user. Alternatively or additionally, computing device 104 may retrieve from a database an applicable inflammatory response label 140 associated with the alimentary element to assist in generating the second inflammation metric 148. Computing device 104 may display to a user, via a user device, the second inflammation metric 148, as described above. Computing device 104 may store and/or retrieve a second inflammation metric 148 from a database, as described in further detail below.

Continuing in reference to FIG. 1, computing device 104 may calculate a numerical difference between a first inflammation metric 120 and a second inflammation metric 148. Computing device 104 may calculate a numerical difference using any suitable mathematical operation, for instance and without limitation, using subtraction. Computing device 104 may calculate a quantitative difference, wherein the difference is a numerical value between two inflammation metrics, for instance wherein the inflammation metrics may differ from changes in diet, changes in time, and the like. Alternatively or additionally, computing device 104 may calculate a quantitative difference wherein the difference is a mathematical expression such as a function, vector, polar coordinate, matrix of values, or the like, wherein the expression describes, for instance and without limitation, a difference between rates of inflammation change between two or more inflammation metrics. In such an example, computing device 104 may inform a user how the inflammation metrics have changed over a longer period of time, wherein a plurality of inflammation metrics has been calculated using a plurality of past user data inputs.

Continuing in reference to FIG. 1, determining the quantitative difference between the first inflammation metric and the second inflammation metric may include determining, using a ranking machine-learning process, if a quantitative difference in inflammation metric is due to changes in changes in user indicated alimentary elements. Ranking machine-learning process may be implemented using any type of machine-learning process and/or algorithm suitable for use as the alimentary element machine-learning process 136. Ranking machine-learning process may be any type of machine-learning process and/or algorithm that may be performed by a machine-learning module, as described in further detail below. Ranking machine-learning process 152 may accept inputs that are quantitative differences between two or more inflammation metrics of a user and determine if the difference is due to an indicated alimentary element, as opposed to a difference due to physiological extraction data. In doing so, ranking machine-learning process 152 may learn which alimentary elements resulted in reduced and/or reversed inflammation in a user.

Continuing in reference to FIG. 1, computing device 104 may catalogue alimentary elements present in the user data that resulted in decreases in inflammation metric, wherein cataloguing includes saving a list 156 of selected alimentary components in a database for a user. In non-limiting exemplary embodiments, cataloguing alimentary elements in this way saves a list 156 of beneficial alimentary elements a user has indicated that he or she preferably consumes and/or uses in recipes. In non-limiting illustrative examples, computing device 104 may recognize user food preferences, predict potential food allergies, hypersensitivities, gut wall interaction, and the like, based on user consumption patterns from the catalogued foods. For instance and without limitation, if a pattern emerges wherein meals and/or foods with gluten, wheat, flour, and the like, result in unusual increases in inflammation, yet a user continues to consume these alimentary elements, computing device 104 may alert a user with inflammation response labels 140 that indicate potential for conditions such as rheumatoid arthritis (RA), celiac disease, gluten intolerance, and the like, and/or suggestions for alimentary elements to replace the items. Alternatively or additionally in non-limiting examples, if a user prefers to eat berries, such as blueberries, blackberries, and raspberries, but not strawberries, computing device 104 may catalogue those alimentary elements in a list 156, and predict that a user abstains from strawberries due to an allergy, and may learn not suggest alimentary elements or recipes that use strawberries.

Continuing in reference to FIG. 1, ranking machine-learning process 152 determining the quantitative difference between the first inflammation metric and the second inflammation metric may include ranking, using the catalogued list, a plurality of alimentary components based on their effect on the user inflammation metric In non-limiting exemplary embodiments, ranking machine-learning process 152 may accept an input of catalogued alimentary elements, and generate a ranked list 160 as an output, wherein generating the ranked list 160 includes use a ranking algorithm to rank alimentary elements based on their impact on reversing inflammation. Ranking may be performing using a ranking process, as described in further detail below.

Figure 2:
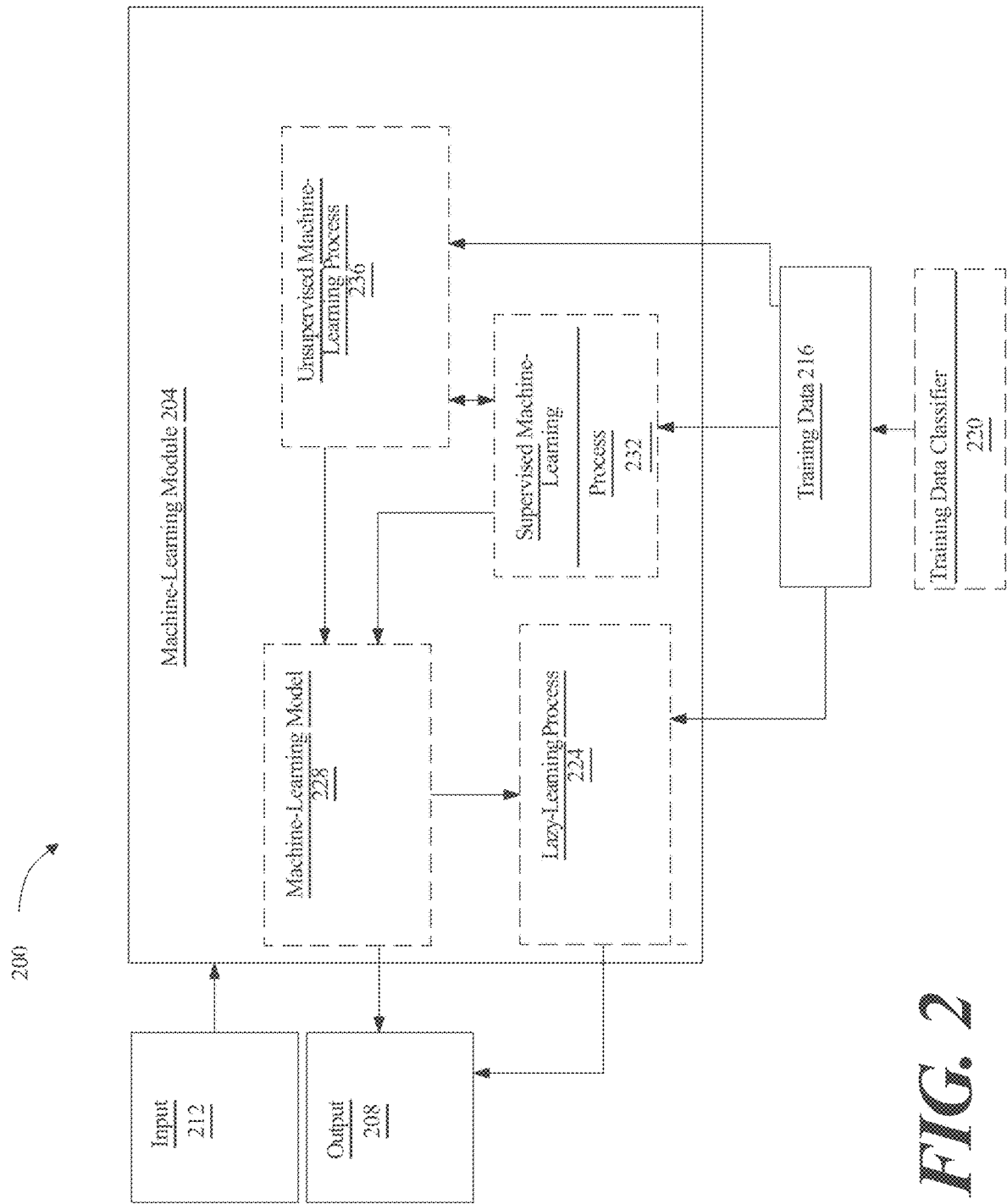
FIG. 2 is a block diagram of an exemplary embodiment of a machine-learning module.

Referring now to FIG. 2 an exemplary embodiment 200 of a machine-learning module 204 that may perform one or more machine-learning processes as described in this disclosure is illustrated. Machine-learning module 204 may include any suitable machine-learning module that may perform determinations, classification, and/or analysis steps, methods, processes, or the like as described in this disclosure using machine-learning processes and/or machine-learning models. A "machine learning process," as used in this disclosure, is a process that automatedly uses training data to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 216 may include a plurality of data entries, each entry representing a set of data elements that were recorded, received, and/or generated together; data elements may be correlated by shared existence in a given data entry, by proximity in a given data entry, or the like. Training data 216 may correspond to at least an element of data entry that may be used for training, a subset of a training data 216, and/or multiple training data sets. Multiple data entries in training data 216 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 216 according to various correlations; correlations may indicate causative and/or predictive links between categories of data elements, which may be modeled as relationships such as mathematical relationships by machine-learning processes as described in further detail below. Training data 216 may be formatted and/or organized by categories of data elements, for instance by associating data elements with one or more descriptors corresponding to categories of data elements. As a non-limiting example, training data 216 may include data entered in standardized forms by persons or processes, such that entry of a given data element in a given field in a form may be mapped to one or more descriptors of categories. Elements in training data 216 may be linked to descriptors of categories by tags, tokens, or other data elements; for instance, and without limitation, training data 216 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 216 may include one or more elements that are not categorized; that is, training data 216 may not be formatted or contain descriptors for some elements of data. Machine-learning algorithms and/or other processes may sort training data 216 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 216 to be made applicable for two or more distinct machine-learning algorithms as described in further detail below. Training data 216 used by machine-learning module 200 may correlate any input data as described in this disclosure to any output data as described in this disclosure. As a non-limiting illustrative example, physiological extraction 108 data input 212 and inflammation metric 120 output 208 determined from training data 216 that relates physiological extraction 108 data to ranges of numerical values that may be used as an inflammation metric 120.

Further referring to FIG. 2, training data may be filtered, sorted, and/or selected using one or more supervised and/or unsupervised machine-learning processes and/or models as described in further detail below; such models may include without limitation a Training data classifier 220. Training data classifier 220 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like.

Machine-learning module 200 may generate a classifier using a classification algorithm, defined as a process whereby a computing device and/or any module and/or component operating thereon derives a classifier from training data 216. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, Training data classifier 220 may classify elements of training data to sections of physiological extraction 108 data as it relates to subsets of users and the corresponding numerical values that result in the inflammation metric 112.

Still referring to FIG. 2, machine-learning module 200 may be configured to perform a lazy-learning process 224 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 216. Heuristic may include selecting some number of highest-ranking associations and/or training data 216 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning model. A "machine-learning model," as used in this disclosure, is a mathematical and/or algorithmic representation of a relationship between inputs 212 and outputs 208, as generated using any computing device, machine-learning module, and/or machine-learning process, including without limitation any process as described above, and stored in memory; an input 212 may be submitted to a machine-learning model 228 once the model is created, which generates an output 208 based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 228 may be generated by creating an artificial neural network, such as a convolutional neural network comprising an input layer of nodes, one or more intermediate layers, and an output layer of nodes. Connections between nodes may be created via the process of "training" the network, in which elements from training data 216 are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 232. At least a supervised machine-learning process 232, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include physiological extraction 108 data, as described above, as inputs, inflammation metrics 120 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 216. Persons skilled in the art, upon reviewing the entirety of this disclosure, will be aware of various possible variations of at least a supervised machine-learning process 232 that may be used to determine relation between inputs and outputs. Supervised machine-learning processes may include classification algorithms as defined above. In further non-limiting illustrative examples, a ranking machine-learning process 152 may be a supervised machine-learning process 228, wherein the machine-learning process performs a scoring function, as described above, to rank input elements and output a list of that has been sorted using the scoring function. In such an example, user data 144 may be input to the ranking machine-learning process 152 to generate a ranked list 160 as an output.

Further referring to FIG. 2, machine learning processes may include at least an unsupervised machine-learning processes 236. An unsupervised machine-learning process 236, as used herein, is a process that derives inferences in datasets without regard to labels; as a result, an unsupervised machine-learning process 236 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 228 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic, or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 216 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 216.

Figure 3:
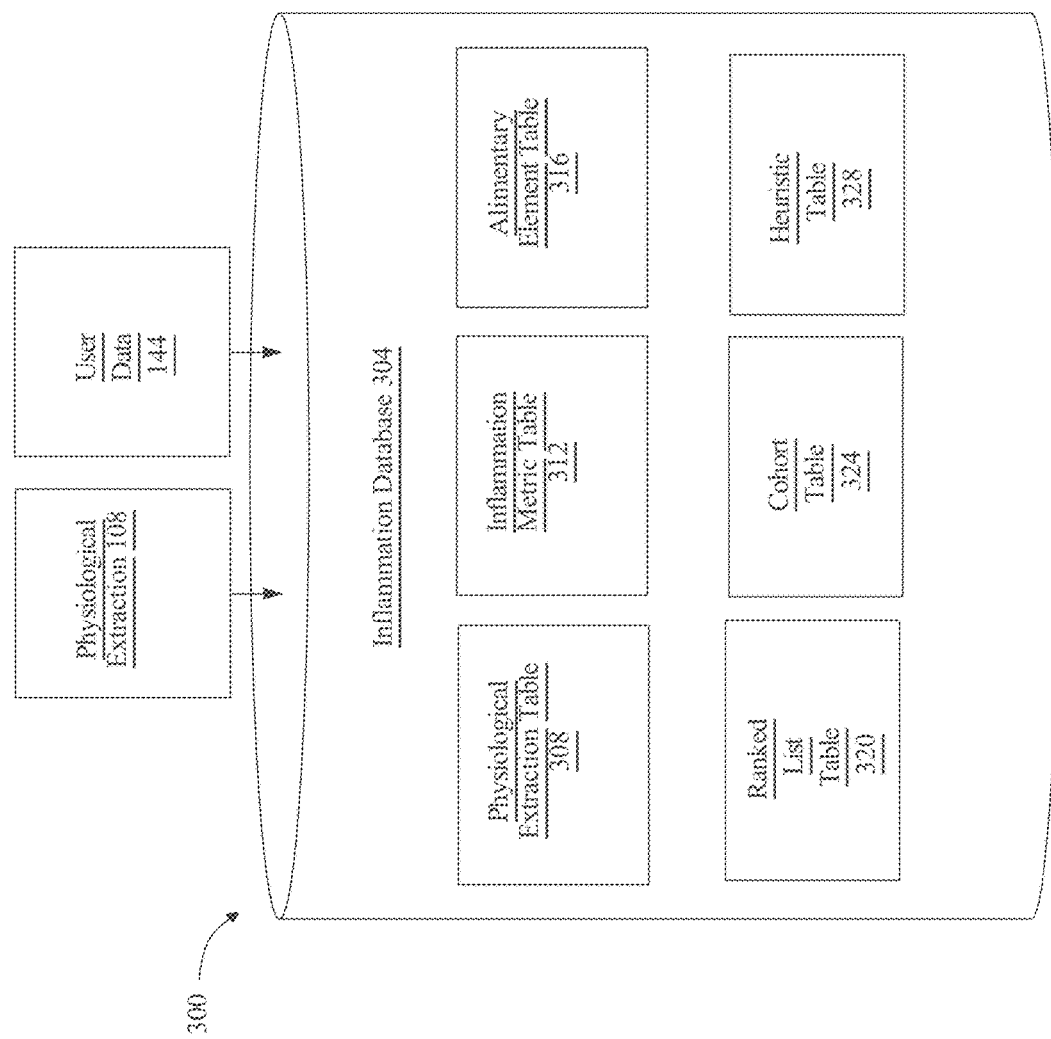
FIG. 3 is a block diagram of an exemplary embodiment of an inflammation database.

Referring not to FIG. 3, a non-limiting exemplary embodiment 300 of database is illustrated. A "database," as used herein may refer to an inflammation database 304. Inflammation database 304 may be implemented, without limitation, as a relational database, a key-value retrieval database such as a NOSQL database, or any other format or structure for use as a database that a person skilled in the art would recognize as suitable upon review of the entirety of this disclosure. Inflammation database 304 may alternatively or additionally be implemented using a distributed data storage protocol and/or data structure, such as a distributed hash table and the like. Inflammation database 304 may include a plurality of data entries and/or records, as described above. Data entries in a inflammation database 304 may be flagged with or linked to one or more additional elements of information, which may be reflected in data entry cells and/or in linked tables such as tables related by one or more indices in a relational database. Inflammation database 304 may be designated as an online repository of data, or other network-integrated data repository. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 3, inflammation database 304 may include, without limitation, a physiological extraction table 308, inflammation metric table 312, alimentary element table 316, ranked list table 320, cohort table 324, and/or heuristic table 328. Determinations by a machine-learning process, machine-learning model, scoring function, and the like, may also be stored and/or retrieved from the inflammation database 304, for instance in non-limiting examples a classifier describing a subset of users with alike physiological extraction data as it relates to inflammation. Determinations by a machine-learning model, for instance for calculating a degradation rate and/or a machine-learning process for determining an antidote strategy, may also be stored and/or retrieved from the inflammation database 304. As a non-limiting example, inflammation database 304 may organize data according to one or more instruction tables. One or more inflammation database 304 tables may be linked to one another by, for instance in a non-limiting example, common column values. For instance, a common column between two tables of inflammation database 304 may include an identifier of a submission, such as a form entry, textual submission, metrics, and the like, for instance as defined above; as a result, a query may be able to retrieve all rows from any table pertaining to a given submission or set thereof. Other columns may include any other category usable for organization or subdivision of expert data, including types of expert data, names and/or identifiers of experts submitting the data, times of submission, and the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of an inflammation database 304 may include, as a non-limiting example, a physiological extraction table 304, which may include elements of user physiological extraction 108 data, as described above, and any associated data relating to inflammation, determinations made by an expert, medical professional, physical trainer, or the like, including medical history data, physiological measurements, mental health, medical conditions, diagnoses, diseases, or any other factors for use in determining inflammation metrics 120, alimentary elements, and/or other elements of data computing device 104 may store, retrieve, and/or use to determine usefulness and/or relevance of physiological extraction 108 data in determining inflammation metrics 120, alimentary elements, and/or user efforts as described in this disclosure.

One or more tables may include, without limitation, inflammation metric table 312, which may include numerical values, functions, vectors, matrices, coordinates, graphical data, parameters, and the like, for instance and without limitation, that link user physiological extraction 108 to ranges of inflammation markers, inflammation metrics, and the like, as described above. Inflammation metric table 312 may contain physiological ranges of inflammation markers, including organization of inflammation markers based on classification as 'systemic' or 'local', as described above.

One or more tables may include, without limitation, alimentary element table 316, which may include alimentary elements, recipes, food items, restaurant menus, meals, and the like, including any associated physiological extraction 108 data. In non-limiting illustrative examples, alimentary element table 316 may include alimentary elements that are organized according to when a user input the data, including for instance timestamps, amounts, and the like, associated with when and how a user consumed the alimentary element.

One or more tables may include, without limitation, a ranked list table 320, which may correlate user alimentary elements to influence an inflammation metric as it pertains to a determinations about inflammation metric 120, alimentary elements, recipes, and the like, including any outcomes, models, heuristics, scores and/or combinations thereof as they may correspond to rankings, determination, calculations, or combinations of catalogued items listed as numerical values, metrics, functions, vectors, matrices, and the like, that corresponds to determining a alimentary elements that may have been cached, catalogued, or otherwise stored.

One or more tables may include, without limitation, a cohort category table 324, which may contain one or more inputs identifying one or more categories of data, for instance demographic data, lifestyle data, physiological data, sleep pattern data, or the like, with regard to which users having matching or similar data may be expected to have similar inflammation metrics 120, alimentary elements, recipes, ranked lists, inflammation markers, or the like, as a result of a machine-learning process determination, machine-learning model, ranking algorithm, and/or other data input and output elements.

One or more tables may include, without limitation, a heuristic table 238, which may include one or more inputs describing potential mathematical relationships between at least an element of user data and, for instance and without limitation, physiological extraction 108 data, inflammation metrics 120, alimentary elements, inflammation markers, and the like, as a result of a machine-learning process determination, machine-learning model, ranking function, and the like, as described above.

Figure 4:
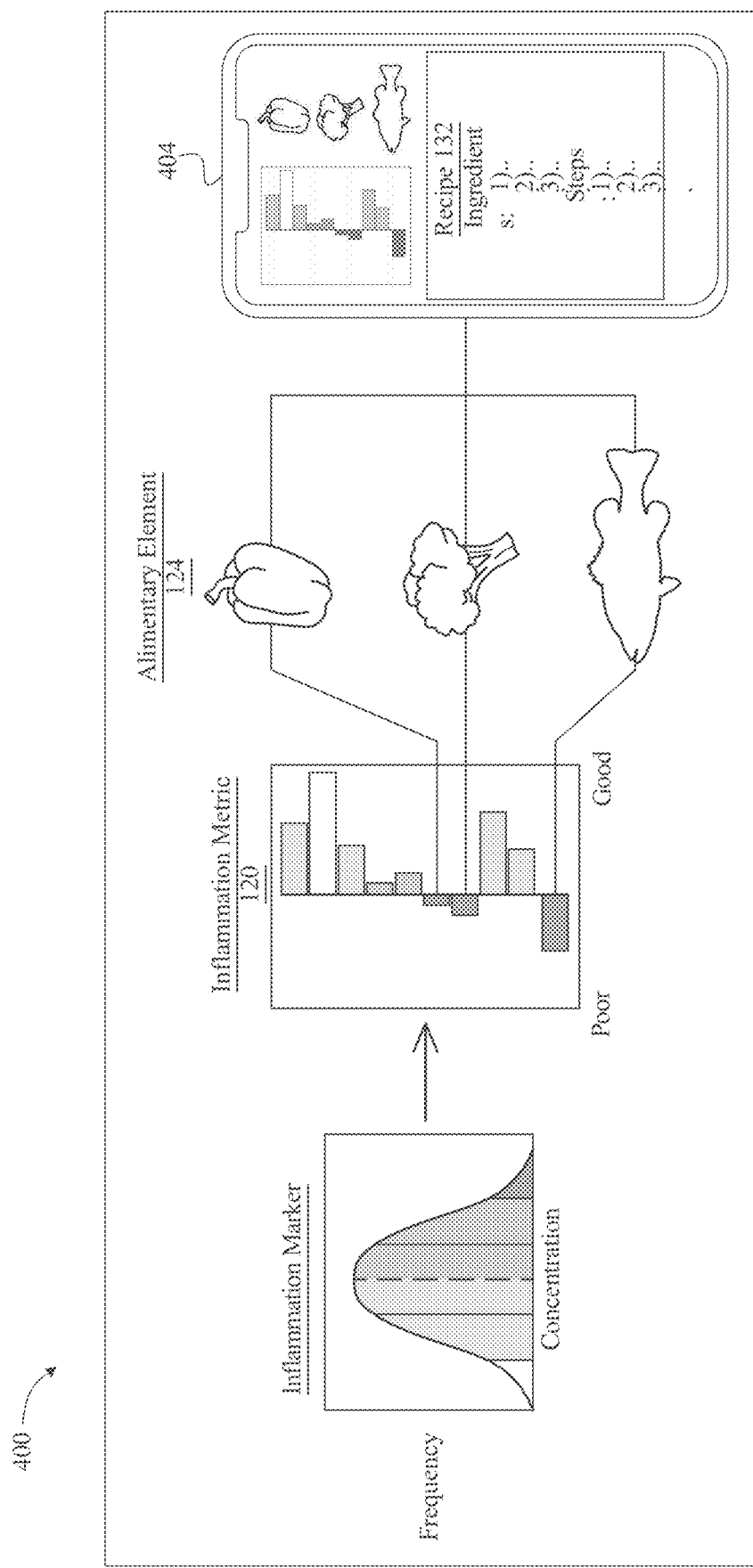
FIG. 4 is a diagrammatic representation of an exemplary embodiment for generating alimentary elements.

Referring now to FIG. 4, a non-limiting exemplary embodiment 400 of a workflow for generating alimentary elements 124 for reversing inflammation in a user. User physiological extraction 108 data may include data regarding an inflammation marker, such as a systemic inflammation marker 112 and/or a local inflammation marker 116. An inflammation machine-learning model 124 may determine a quantitative measure of a user's inflammation marker and assign an inflammation metric 120. In non-limiting illustrative examples, as shown in FIG. 4, there may be a normal distribution of concentration of an inflammation marker, such as IL-6, found in blood draws, wherein there is an equal distribution of frequency of concentrations about a mean value (denoted as the dashed line). In such an example, users may fall somewhere on the normal distribution wherein the machine-learning model may assign an inflammation metric 120 according to where the user falls, for instance highest score for lower concentration (white area under curve) to a lower score for higher concentrations of inflammatory marker (gradation of light grey to dark grey). For instance and without limitation, a user may have a quantitative measure that relates to a 'good', or healthy level of inflammatory marker, or 'poor', a higher level of an inflammatory marker that may signify a health concern. According to a user's inflammation metric 120, alimentary element machine-learning process 136 may identify at least an alimentary element 124 that can reverse inflammation in the user. These alimentary elements may be provided to a user, via a user device 404. In non-limiting illustrative examples, alimentary elements may be provided to reverse inflammation where there are indications of inflammation. Alternatively or additionally, alimentary elements may be suggested for swapping to 'better' alimentary element choices to prevent a 'good' inflammation metric 120 from getting worse.

Figure 5:
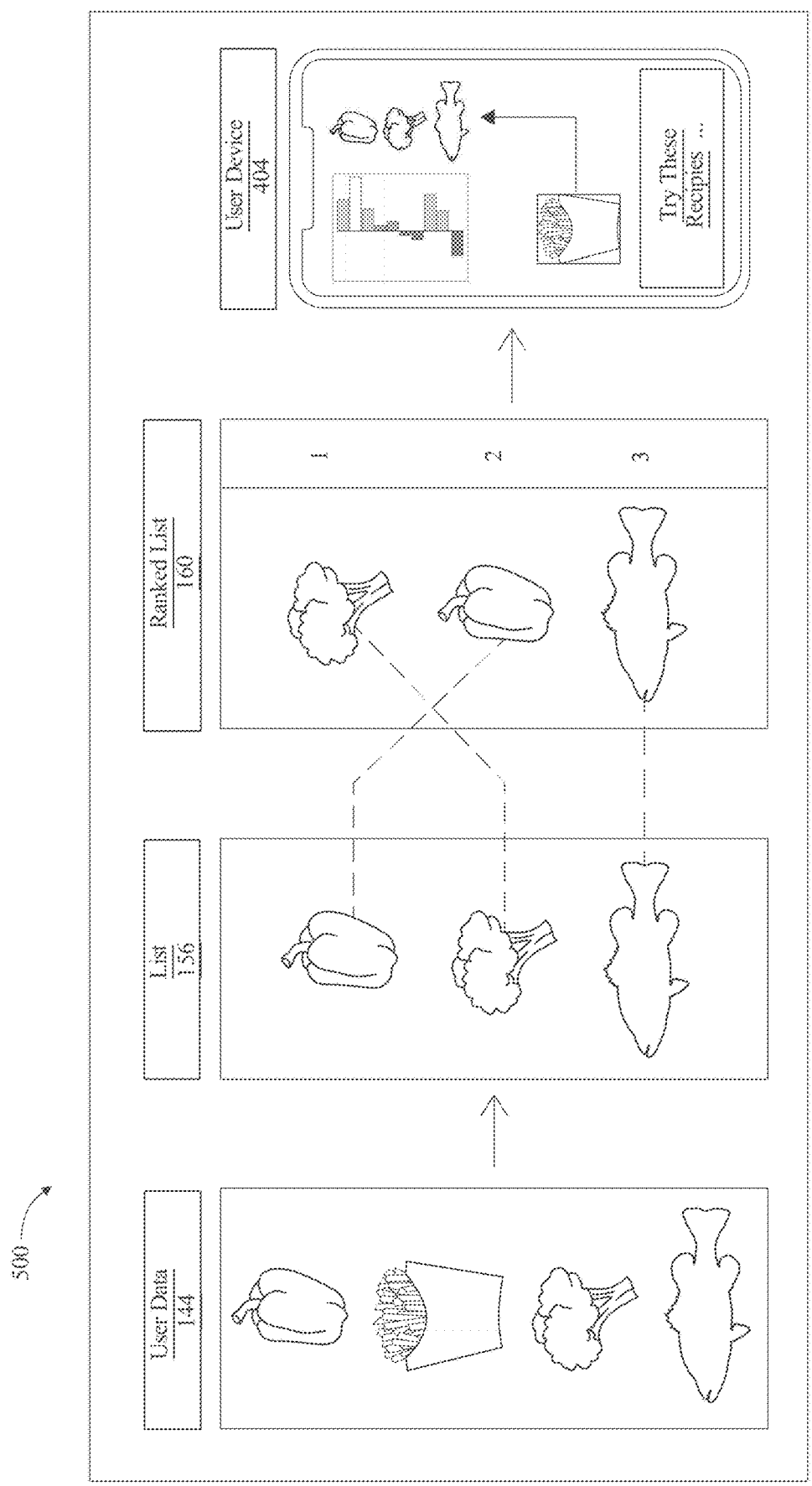
FIG. 5 is a diagrammatic representation of an exemplary embodiment of user data catalogued into a list to generate a ranked list.

Referring now to FIG. 5, a non-limiting exemplary embodiment 500 of user data 144 catalogued into a list 156 to generate a ranked list 160 to provide to a user device 404 is illustrated. User data 144 may be provided via a user device and/or retrieved from an inflammation database 304. Ranking machine-learning process 152 may catalogue a list 160 of alimentary elements based on the calculated effect of the alimentary elements on inflammation metric 120. Ranking machine-learning process 152 may use an inflammatory response label 140 to sort items into the list 156. Ranking machine-learning process 152 may generate a ranked list 160 of alimentary elements, wherein elements are ranked based on their effect on inflammation metric 120. Ranked list 160 may be provided via a user device so that a user may make an informed choice. Alternatively or additionally, computing device 104 may store and/or retrieve alimentary elements of the ranked list 160 and use the elements to identify and retrieve a recipe.

Figure 6:
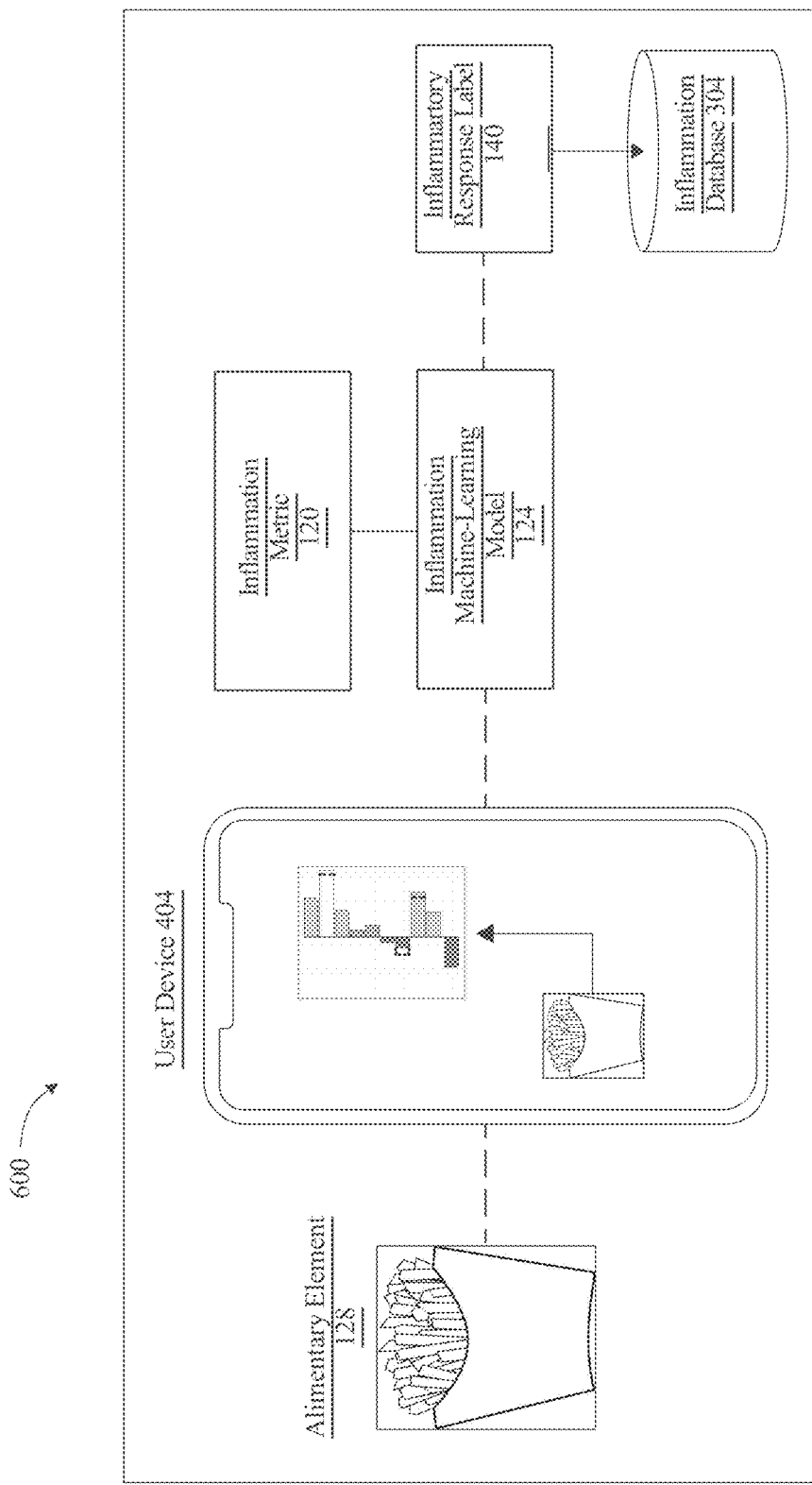
FIG. 6 is a diagrammatic representation of an exemplary embodiment of generating an inflammatory response label using an inflammation machine-learning model.

Referring now to FIG. 6, a non-limiting exemplary embodiment 600 of generating an inflammatory response label 140 using an inflammation machine-learning model 124 is illustrated. Inflammatory response label 140 may be a quantitative measurement of the inflammatory response a user may have to an alimentary element. A user may input an alimentary element via a user device 404, and the inflammation machine-learning model 124 may determine how this alimentary element will affect the inflammation metric 120. Such a process will result in an inflammatory response label 140 for that alimentary element for that user and may be stored and/or retrieved from an inflammation database 304.

Figure 7:
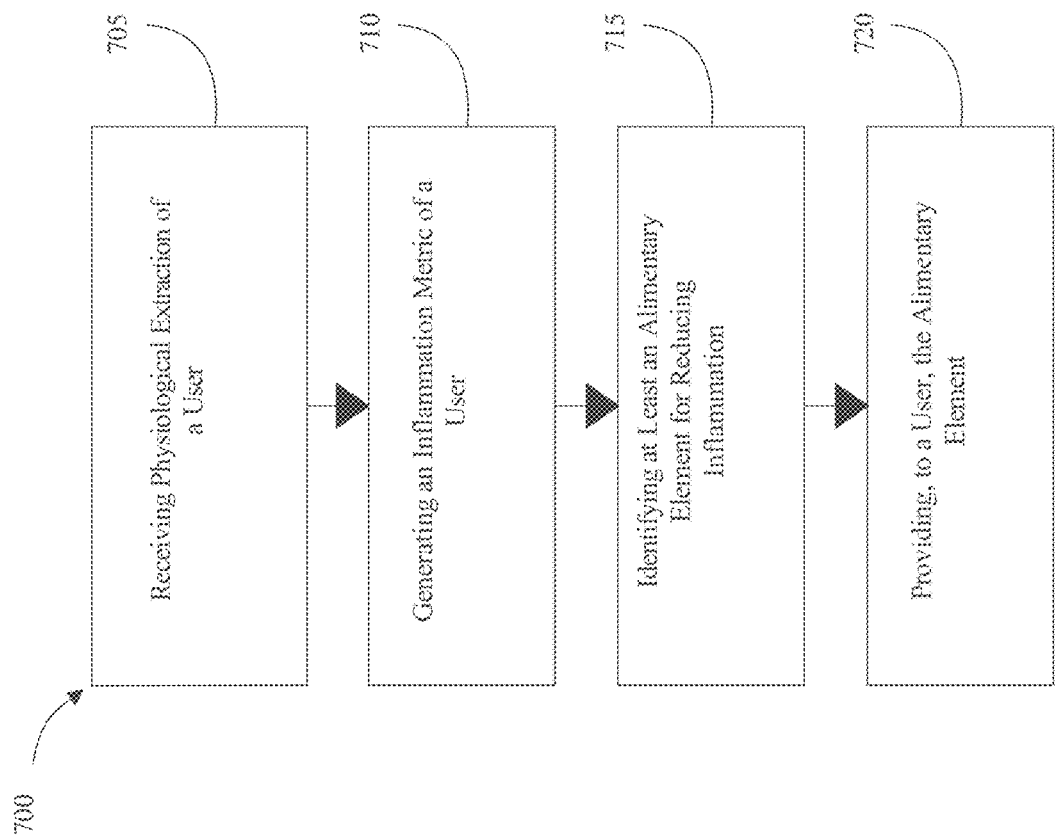
FIG. 7 is a flow diagram illustrating an exemplary workflow of a method for reversing inflammation in a user.

Referring now to FIG. 7, a non-limiting exemplary embodiment of a method 700 of reversing inflammation in a user is illustrated. At step 705, computing device 104 is configured for receiving physiological extraction 108 of a user, wherein physiological extraction 108 contains at least an inflammation marker. At least an inflammation marker further comprises a systemic inflammation marker 112. At least an inflammation marker further comprises a local inflammation marker 116; this may be implemented, without limitation, as described above in FIG. 1-6.

At step 710, computing device 104 is configured for generating an inflammation metric 120 of a user, wherein generating the inflammation metric 120 may include using an inflammation machine-learning model 124, the inflammation machine-learning model 124 trained using training data 216 that enumerates hallmarks of inflammation in a user with quantitative measurements of inflammation; this may be implemented, without limitation, as described above in FIG. 1-6.

At step 715, computing device 104 is configured for identifying, as a function of the inflammation metric 120 and an alimentary element machine-learning process 136, at least an alimentary element 128 for reversing inflammation in the user. Determining the at least an alimentary element 128 for the user may include querying for a suitable alimentary element 128 for reversing inflammation in the user as a function of the at least an inflammation marker. Querying for a suitable alimentary element 128 may include using the alimentary element machine-learning process 136 to identify at least a recipe 132 for the suitable alimentary element 128, wherein the recipe 132 reduces the at least an inflammation marker; this may be implemented, without limitation, as described above in FIG. 1-6.

At step 720, computing device 104 is configured for providing, to the user, the at least an alimentary element 128 for reversing inflammation. Providing to the user the at least an alimentary element 128 for reversing inflammation may include conveying the at least an alimentary element 128 amount to a user device 304, and receiving a user input from the user device 304. Receiving, user input from the user device, may include a first alimentary element. Determining, using the inflammation machine-learning model 124 and the first alimentary element, the effect of the first alimentary element on the inflammation metric 120 of the user, and generating an inflammatory response label 140 as a function of determining the affect. Computing device 104 may be further configured to receive a plurality of inflammation measurements, establish at least an alimentary element for reversing inflammation in the plurality of inflammation measurements, and generate, by querying a database, at least a recipe for the plurality of alimentary components that do not contribute to inflammation in the plurality of inflammation measurements, and provide, to the user, the recipe. Computing device 104 may be further configured to receive user data 144, wherein user data 144 is more current in time than a first provided alimentary element 128 and contains at least an alimentary element selected by user, generate, using the inflammation machine-learning model 124 and the user data 144, a second inflammation metric, and calculate a quantitative difference between a first inflammation metric and a second inflammation metric. Determining the quantitative difference between the first inflammation metric and the second inflammation metric may include determining, using a ranking machine-learning process 152, if a quantitative difference in inflammation metric 120 is due to changes in user indicated alimentary elements, cataloguing alimentary elements present in the user data 144 that resulted in decreases in inflammation metric 120, wherein cataloguing includes saving a list of selected alimentary components in a database for a user, and ranking, using the ranking machine-learning process and the catalogued list, a plurality of alimentary components based on their effect on the user inflammation metric; this may be implemented, without limitation, as described above in FIG. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
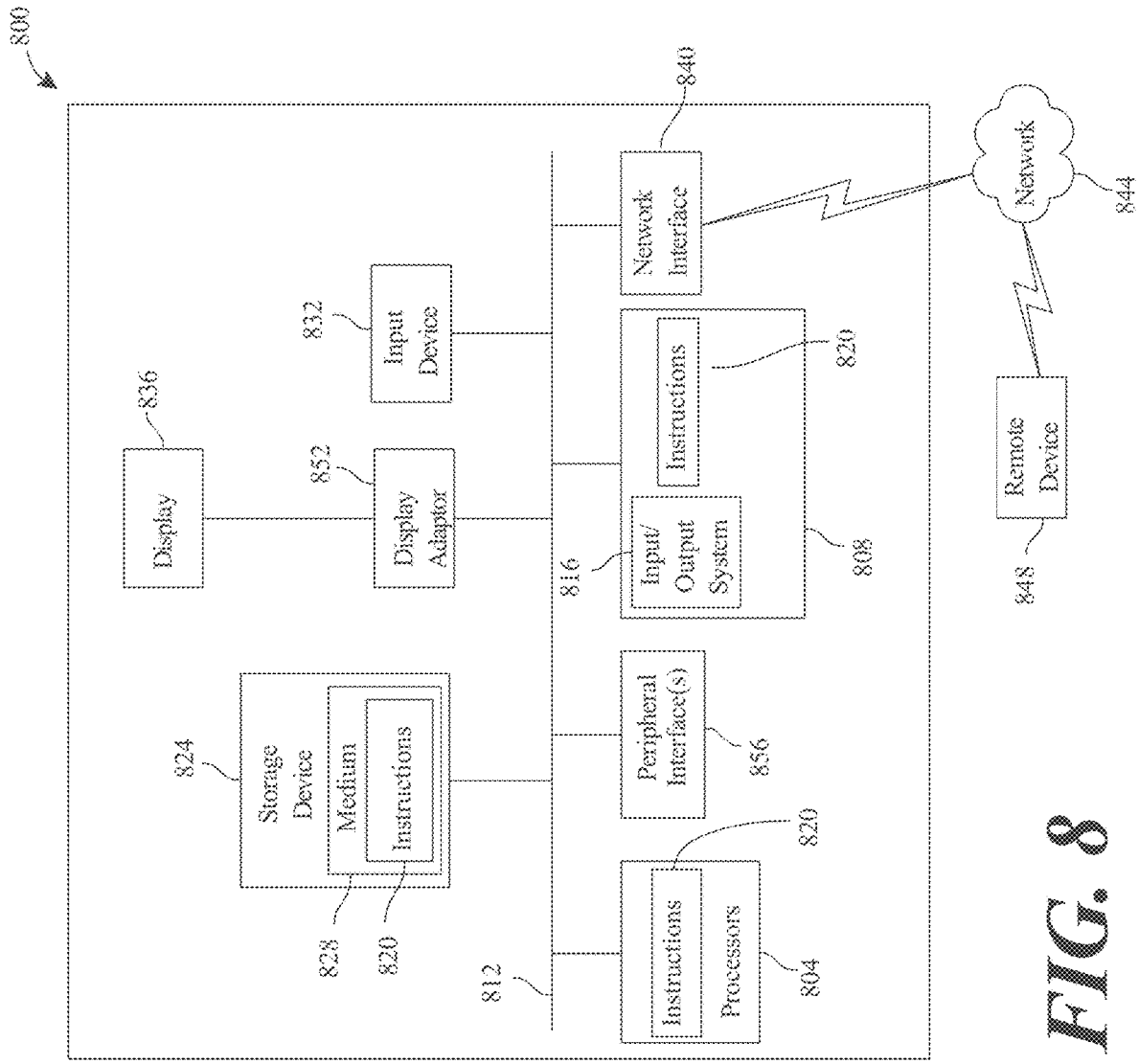
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for matching inflammation compatibility of a group of users, wherein the system comprises a computing device configured to:
   receive a first physiological extraction of at least a user of a plurality of users, wherein the first physiological extraction contains at least an inflammation marker;
   generate a first inflammation metric of the at least a user, wherein generating the first inflammation metric further comprises:
      training an inflammation machine-learning model as a function of inflammation metric training data, wherein the inflammation metric training data includes a plurality of entries correlating physiological extraction data of the at least a user to at least an inflammation metric that quantitates hallmarks of inflammation in the at least a user; and
      generating the first inflammation metric as a function of the inflammation machine-learning model and the first physiological extraction of the at least a user input; and
   provide the first inflammation metric to the at least a user;
   generate, using the inflammation machine-learning model, at least a second inflammation metric, wherein user data and the first inflammation metric are inputted, and the second inflammation metric is outputted, wherein user data comprises at least an alimentary element and a second physiological extraction, wherein a second physiological extraction is more recent than a first physiological extraction and wherein the second inflammation metric reflects changes in inflammation compared to the first inflammation metric due to the at least an alimentary element consumed by the user;
   identify, using the comparison of the first inflammation metric and the at least a second inflammation metric, at least an alimentary element that reversed inflammation in the at least a user, wherein identifying the at least an alimentary element comprises:
      identifying at least an alimentary element from an alimentary catalogue;
      calculating a quantitative difference between the first inflammation metric and the second inflammation metric; and
      determining an alimentary element of the alimentary catalogue that corresponds to the at least an alimentary element consumed that resulted in a reduction of inflammation; and
   provide a representation of the alimentary element of the alimentary catalogue for reversing inflammation of the group of users within a graphical user interface.

2. The system of claim 1, wherein the computing device is further configured to query alimentary elements as a function of the comparison of the first inflammation metric to the at least a second inflammation metric.

3. The system of claim 1, wherein the computing device is further configured to provide a recipe that reverses inflammation of a plurality of users.

4. The system of claim 1, wherein the computing device is further configured to substitute the at least an initial alimentary element with a substitute alimentary element as a function of the comparison of the first inflammation metric to the at least a second inflammation metric.

5. The system of claim 1, wherein identifying the at least an alimentary element further comprises calculating a minimal effect that using the at least an alimentary element has on the first inflammation metric and the second inflammation metric using a minimization model.

6. The system of claim 1, wherein the computing device is further configured to:
   determine a user consumption pattern;
   calculate an effect the user consumption pattern has on a user inflammation metric; and
   update the alimentary catalogue as a function of the calculated effect.

7. The system of claim 1, wherein the computing device is further configured to:
   generate the alimentary catalogue, wherein the alimentary catalogue includes alimentary elements present in user data that resulted in decreases in inflammation metric, wherein cataloguing includes saving a list of selected alimentary components in a database for a user;
   rank, using a ranking machine-learning process and the list, a plurality of alimentary components based on their effect on the user inflammation metric; and
   provide, to the user, the ranked alimentary elements for reversing inflammation.

8. The system of claim 1, wherein the computing device is further configured to classify, using a user classification model, physiological extraction of the at least a user to a user cohort.

9. The system of claim 8, wherein identifying the at least an alimentary element further comprises comparing the at least an alimentary element to the user cohort.

10. The system of claim 1, wherein the computing device is further configured to identify at least an alimentary element that is correlated with a quantitative difference.

11. A method of matching inflammation compatibility of a group of users using a computing device, comprising:
   receiving a first physiological extraction of at least a user of a plurality group of users, wherein the first physiological extraction contains at least an inflammation marker;
   generating a first inflammation metric of the at least a user, wherein generating the first inflammation metric further comprises:
      training an inflammation machine-learning model as a function of inflammation metric training data, wherein the inflammation metric training data includes a plurality of entries correlating physiological extraction data of the at least a user to at least an inflammation metric that quantitates hallmarks of inflammation in the at least a user; and
      generating the first inflammation metric as a function of the inflammation machine-learning model and the first physiological extraction of the at least a user input; and
   providing the first inflammation metric to the at least a user;
   generating, using the inflammation machine-learning model, at least a second inflammation metric, wherein user data and the first inflammation metric are inputted, and the second inflammation metric is outputted, wherein user data comprises at least an alimentary element and a second physiological extraction, wherein a second physiological extraction is more recent than a first physiological extraction and wherein the second inflammation metric reflects changes in inflammation compared to the first inflammation metric due to the at least an alimentary element consumed by the user;
   identifying, using the comparison of the first inflammation metric and the at least a second inflammation metric, at least an alimentary element that reversed inflammation in the at least a user, wherein identifying the at least an alimentary element comprises:
identifying at least an alimentary element from an alimentary catalogue;
calculating a quantitative difference between the first inflammation metric and the second inflammation metric; and
determining an alimentary element of the alimentary catalogue that corresponds to the at least an alimentary element consumed that resulted in a reduction of inflammation; and
providing a representation of the alimentary element of the alimentary catalogue for reversing inflammation of the group of users within a graphical user interface.

12. The method of claim 11, wherein the computing device is further configured to query alimentary elements as a function of the comparison of the first inflammation metric to the at least a second inflammation metric.

13. The method of claim 11, wherein the computing device is further configured to provide a recipe that reverses inflammation of a plurality of users.

14. The method of claim 11, wherein the computing device is further configured to substitute at least an alimentary element with a substitute alimentary element as a function of the comparison of the first inflammation metric to the at least a second inflammation metric.

15. The method of claim 11, wherein identifying the at least an alimentary element further comprises calculating a minimal effect that using the at least an alimentary element has on the first inflammation metric and the second inflammation metric using a minimization model.

16. The method of claim 11, wherein the computing device is further configured to:
determine a user consumption pattern;
calculate an effect the user consumption pattern has on a user inflammation metric; and
update the alimentary catalogue as a function of the calculated effect.

17. The method of claim 11, wherein the computing device is further configured to:
generate the alimentary catalogue, wherein the alimentary catalogue includes alimentary elements present in user data that resulted in decreases in inflammation metric, wherein cataloguing includes saving a list of selected alimentary components in a database for a user;
rank, using a ranking machine-learning process and the list, a plurality of alimentary components based on their effect on the user inflammation metric; and
provide, to the user, the ranked alimentary elements for reversing inflammation.

18. The method of claim 11, wherein the computing device is further configured to classify, using a user classification model, physiological extraction of the at least a user to a user cohort.

19. The method of claim 18, wherein identifying the at least an alimentary element further comprises comparing the at least an alimentary element to the user cohort.

20. The method of claim 11, wherein identifying the at least an alimentary element further comprises identifying an alimentary element that is correlated with quantitative difference.

* * * * *